(12) United States Patent
Stockert et al.

(10) Patent No.: US 11,200,971 B2
(45) Date of Patent: Dec. 14, 2021

(54) SECURE TOKEN IDENTIFICATION AND MEDICAL RULE-BASED AUTHORIZATION SYSTEM

(71) Applicant: Health2047, Inc., Menlo Park, CA (US)

(72) Inventors: Jack Stockert, Los Altos, CA (US); Charles Aunger, Hayward, CA (US); Neile Grayson, Mercer Island, WA (US); Roel Nuyts, San Francisco, CA (US); Doug Given, Menlo Park, CA (US)

(73) Assignee: Health2047, Inc., Menlo Park, CA (US)

( * ) Notice: Subject to any disclaimer, the term of this patent is extended or adjusted under 35 U.S.C. 154(b) by 272 days.

(21) Appl. No.: 16/104,809

(22) Filed: Aug. 17, 2018

(65) Prior Publication Data
US 2019/0057763 A1 Feb. 21, 2019

Related U.S. Application Data

(60) Provisional application No. 62/546,739, filed on Aug. 17, 2017.

(51) Int. Cl.
*G16H 20/10* (2018.01)
*G16H 10/60* (2018.01)
(Continued)

(52) U.S. Cl.
CPC ............ *G16H 20/10* (2018.01); *G06F 21/30* (2013.01); *G06F 21/31* (2013.01); *G16H 10/00* (2018.01);
(Continued)

(58) Field of Classification Search
CPC ........ G16H 20/10; G16H 10/00; G16H 20/00; G16H 10/60; G06F 21/30; G06F 21/31; G06F 21/32
See application file for complete search history.

(56) References Cited

U.S. PATENT DOCUMENTS 6,315,720 B1  11/2001  Williams et al.
6,561,977 B2   5/2003  Williams et al.
(Continued)

FOREIGN PATENT DOCUMENTS

WO   WO-2017083517 A1 *  5/2017  ........... G06Q 10/087

OTHER PUBLICATIONS

Dineen, The Good, The Deviant, and The Human: Exploring Select Provider and Systems Barriers To Appropriate Treatment and Prescribing Practices for Patients in Pain, 2015, ProQuest LLC, pp. 1-296. (Year: 2015).*

*Primary Examiner* — Christopher L Gilligan
(74) *Attorney, Agent, or Firm* — Knobbe, Martens, Olson & Bear, LLP

(57) ABSTRACT

Systems and methods for rapid importation of data including temporally tracked object recognition. One of the methods includes receiving a request to authorize a prescription for a patient, the request being from a medical professional and the request being received of a network. The request is determined to be approved based on information associated with the patient. Transaction information is generated that is associated with the prescription, the transaction information specifying that the patient is authorized to obtain an associated pharmaceutical, and the transaction information being included in a transaction record associated with the patient. Authorization information associated with the prescription is generated, the authorization information being provided to a user device of the patient, and the authorization information enabling confirmation by an outside system that the prescription is authorized. Speech information associated with the prescription is presented on the user device of the patient, such that upon confirmation of presentation of the speech information, the transaction record associated with the patient is updated.

20 Claims, 7 Drawing Sheets

(51) Int. Cl.
*G16H 10/00* (2018.01)
*G16H 20/00* (2018.01)
*G06F 21/30* (2013.01)
*G06F 21/31* (2013.01)
*G06F 21/32* (2013.01)

(52) U.S. Cl.
CPC ............. *G16H 10/60* (2018.01); *G16H 20/00* (2018.01); *G06F 21/32* (2013.01)

(56) References Cited

U.S. PATENT DOCUMENTS

| | | |
|---|---|---|
| 6,755,784 B2 | 6/2004 | Williams et al. |
| 6,869,399 B2 | 3/2005 | Williams et al. |
| 7,141,018 B2 | 11/2006 | Williams et al. |
| 7,959,566 B2 | 6/2011 | Williams et al. |
| 8,315,886 B2 | 11/2012 | Williams et al. |
| 8,626,531 B2 | 1/2014 | Williams et al. |
| 2002/0052543 A1 | 5/2002 | Williams et al. |
| 2003/0149345 A1 | 8/2003 | Williams et al. |
| 2004/0152959 A1 | 8/2004 | Williams et al. |
| 2011/0082707 A1 | 4/2011 | Williams et al. |
| 2012/0046968 A1 | 2/2012 | Kaminski et al. |
| 2012/0316894 A1 | 12/2012 | Williams et al. |
| 2013/0046554 A1 | 2/2013 | Williams et al. |
| 2014/0012600 A1* | 1/2014 | Domesek ............ G06F 19/3456 705/3 |
| 2014/0322683 A1* | 10/2014 | Baym ..................... G09B 5/00 434/219 |
| 2015/0193581 A1 | 7/2015 | Kaminski et al. |
| 2017/0076058 A1* | 3/2017 | Stong .................... G16H 70/40 |
| 2017/0147783 A1* | 5/2017 | Carroll ............... G06F 19/3456 |
| 2017/0344724 A1* | 11/2017 | Nockley ............ G06F 19/3462 |
| 2018/0130050 A1* | 5/2018 | Taylor ................... H04L 9/3247 |
| 2018/0139043 A1* | 5/2018 | Jayachandran ....... H04L 9/3236 |
| 2018/0174673 A1* | 6/2018 | DeFrank ................ G16H 80/00 |
| 2018/0253682 A1* | 9/2018 | Gilman ............. G06Q 20/3825 |

* cited by examiner

SECURE TOKEN IDENTIFICATION AND MEDICAL RULE-BASED AUTHORIZATION SYSTEM

CROSS-REFERENCE TO RELATED APPLICATIONS

This application claims priority to U.S. Prov. App. 62/546,739, and hereby incorporates the provisional application by reference for all purposes. Any and all applications for which a foreign or domestic priority claim is identified in the Application Data Sheet as filed with the present application are hereby incorporated by reference under 37 CFR 1.57.

This application hereby additionally incorporates by reference U.S. Patent Pub. 2018/0211059, which was filed on Jan. 23, 2018 and which claims priority at least to U.S. Prov. App. 62/510,160 filed on May 23, 2017, in its entirety for all purposes.

TECHNICAL FIELD

The present disclosure relates to systems and techniques for security, data integration, and visualization. More specifically, this disclosure relates to secure identification of computing systems and authorizing actions based on transference of secure information.

BACKGROUND

Patient health records are invaluable in determining a patient's current health state and future health risk indicators. Medical information and associated health records, however, are generated using complex disparate proprietary systems and stored in different locations making it difficult to access and compile. Existing systems also often provide inconsistent access to stored medical information. For example, a hospital may have many different proprietary computer systems that each separately record and maintain iedical information of patients in unique proprietary formats. A medical professional can access the medical information, but only on specific computer systems in specific wards of the hospital. This often results in requests for hard copies of medical information pulled one at a time from various storage systems by a variety of personnel, causing significant wait times.

Complicating the provisioning of healthcare, a medical professional may have limited access to the sum total medical information associated with a patient. For example, a patient may have medical information stored at multitudes of hospitals. In this example, the medical professional may not have access to, or be unaware of, medical information at the multitudes of hospitals. As another example, the patient may visit a series of emergency rooms for healthcare, and information from these series of visits may not be accessible to all medical professionals who see the patient. With respect to a particular class of pharmaceuticals, such as pain medication, this inaccessibility of a patient's medical history can create problems for medical professionals. For example, a medical professional may prescribe a pharmaceutical in the particular class to a patient, without knowing the extent to which the patient has received other prescriptions for a similar pharmaceutical.

A patient who has received a valid prescription, and thus has been authorized to obtain the associated pharmaceutical, may encounter obstacles to obtaining the pharmaceutical. For example, while at a pharmacy the patient may be required to prove his/her identity to a pharmacy. Additionally, the pharmacy may further require proof that the authorization was validly granted by a medical professional. As an example, the pharmacy may require that the prescription be confirmed with the medical professional. While these proving steps may guard against improper access to pharmaceuticals, the prescription therefore may not enable a patient to quickly obtain his/her authorized pharmaceutical. Existing systems and schemes lack the technical solutions to enable automatic proof of identification of the patient to the pharmacy, and automatic determination of the patient's valid authorization to obtain a pharmaceutical.

SUMMARY

Particular embodiments of the subject matter described in this specification can be implemented so as to realize one or more of the following advantages. A system described herein can securely safeguard sensitive medical information of patients, while tightly integrating with systems of patients, medical professionals, pharmaceutical companies, and so on, to enable actions. As will be described, the actions enabled by the system can be based on strict adherence to authorization information. An example action can include authorizing a medical professional's prescription of a pharmaceutical to a particular patient. Another example action can include providing authorization information to the particular patient's user device (e.g., mobile device) confirming the authorized prescription. In this way, the particular patient can enter a pharmacy, and utilizing the authorization information on his/her user device, can rapidly obtain an associated pharmaceutical. The authorization information can confirm that the prescription was validly approved, and the user device can confirm an identity of the particular patient (e.g., via biometric identification). Examples of authorization information include authorization tokens, encrypted or otherwise signed information, and so on.

The system described herein can further ensure that a totality of a patient's medical information is automatically analyzed prior to a prescription being authorized to a patient. The system can access disparate medical information, and automatically analyze the medical information to ensure that the prescription is not associated with contraindications. Additionally, the system can ensure that a prescription associated with a particular class of pharmaceuticals (e.g., painkillers) can be properly prescribed to a patient. As an example, the system can identify whether the patient has visited other medical professionals, emergency rooms, hospitals, and so on, to acquire pharmaceuticals in the particular class.

In accessing patient medical information, the system can optionally ensure strict trust conditions are enforced regarding visibility of the patient medical information. As will be described below, the system can allow patients to 'trust' medical professionals and thereby provide access to specific portions (or the entirety) of the patient's medical records and history. The trust can therefore enable a medical professional to review detailed medical information of a patient. However, the system may similarly constrain access to portions of the patient's medical information. For example, while the system can analyze medical information prior to authorizing a prescription, the system can limit an extent to which a medical professional can view the analyzed medical information. That is, the system may indicate to the medical professional that a pharmaceutical is associated with particular contraindications, but may limit access to more detailed medical information of a patient.

For particular pharmaceuticals, a pharmaceutical company may require that particular speech is presented (e.g., read aloud, shown) to a patient. As an example, particular cancer or narcotic drugs may require warnings, and so on, be presented to a patient. In contrast to example current methods, in which a pharmaceutical company may be required to telephone a patient to ensure that particular speech was read to the patient, the system can automatically ensure that a particular patient was presented the required speech. Indeed, the system can ensure that the speech was presented on the particular patient's user device, and that the patient confirmed the presentation. In this way, the system can enable an end-to-end scheme for ensuring speech, such as information, questions for patients to respond to, and so on, can confidently be presented to patients.

As will be described, the system can maintain communications with pharmaceutical systems, which can push updated speech rules associated with their pharmaceuticals to the system. As an example, the system can receive information from a medical professional indicating that a patient is to be prescribed 'Pharmaceutical A'. The system can then obtain rules associated with 'Pharmaceutical A' from an associated pharmaceutical company. Example rules may include the patient being required to read particular information, watch a video, respond to questions, and so on. The system can authorize the prescription upon satisfaction of the rules.

Similarly, the system may de-authorize a prescription provided to a patient's user device upon violation of one or more rules. As an example, the patient may be required to routinely communicate with his/her medical professional, or perform a particular action such as measuring blood glucose levels, recording his/her weight, and so on. The system may de-authorize a prescription such that the patient is unable to fill the prescription at a pharmacy. For example, the system may de-authorize an authentication token stored on the patient's user device, or may update stored information reflecting the de-authorization.

In this way, the systems and methods improve the functioning of the computer and recite technical benefits. For example, the system can strictly adhere to precise authorization rights, such that users (e.g., patients) can rapidly perform actions. Without the techniques described herein, pharmaceutical companies would be required to establish complex systems and methods for ensuring observance of rules associated with their pharmaceuticals. As an example, a pharmaceutical company may otherwise need to contact a patient to ensure that particular information was provided to them. Similarly, the pharmaceutical company may need to approve prescriptive use of particular pharmaceuticals, and ensure that medical professionals, pharmacies, and so on, closely follow these rules. In contrast, the system herein solves such technical deficiencies through utilization of authorization information.

Additionally, a patient operating his/her user device can view all authorized prescriptions and optionally other medical information. Through simple interactions with the user device, and via use of the system, pharmacies can reduce frictions associated with issuing pharmaceuticals. That is, automatic processes to (1) validly identify the patient, and (2) ensure the patient has authorization to obtain a pharmaceutical, can be easily implemented. As will be described, the system can effectively issue credits, and debits, to patients that are associated with prescriptions. In this way, the pharmacy can rapidly receive an indication from the system that the validly identified patient is presently authorized to obtain an associated pharmaceutical. Similarly, the system may de-authorize a prescription, for example via a debit, and the issuance of the prescription may blocked in substantially real-time to de-authorization.

Accordingly, in various embodiments, large amounts of data are automatically and dynamically calculated interactively in response to user inputs, and the calculated data can be efficiently and compactly presented to a user by the system. Thus, in some embodiments, the user interfaces described herein are more efficient as compared to previous user interfaces in which data is not dynamically updated and compactly and efficiently presented to the user in response to interactive inputs.

Further, as described herein, the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

DETAILED DESCRIPTION

Figure 1A:
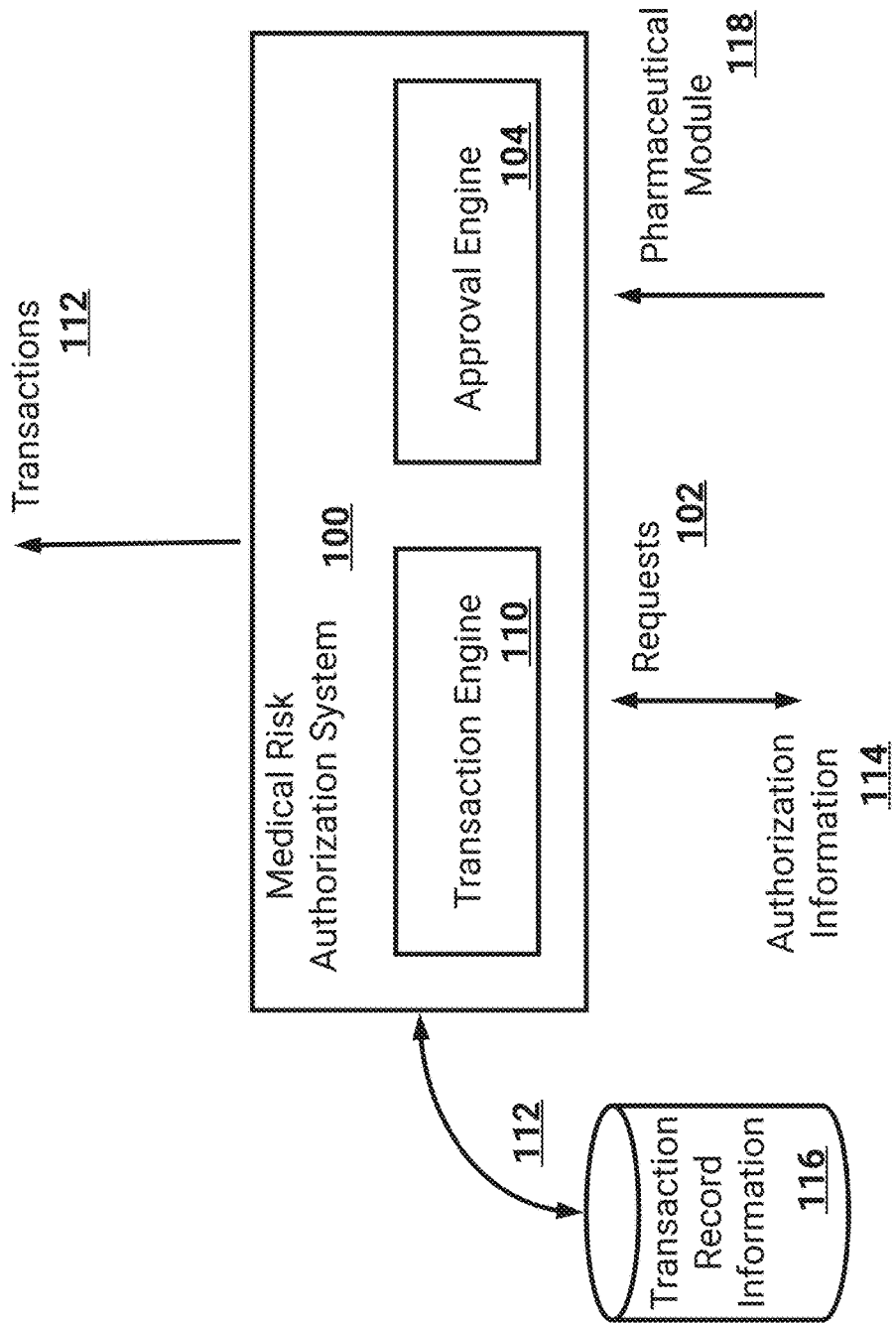
FIG. 1A illustrates an example of a medical authorization system.

This specification describes a system (e.g., the medical risk authorization system 100 described below) that can interface between patients, medical professionals, pharmaceutical entities, payers (e.g., insurance entities), and so on. As will be described, the system can authorize prescriptions from medical professionals to patients. For example, a medical professional can indicate that a particular pharmaceutical is to be prescribed to a patient, and the system can analyze the patient's medical information to authorize the prescription. Additionally, the system can enable pharmaceutical entities (e.g., pharmaceutical companies, such as manufacturers) to specify one or more rules regarding controlled speech for particular pharmaceuticals. As an example, upon receipt of a request to authorize a particular pharmaceutical to a patient, the system can obtain rules associated with the particular pharmaceutical. As will be described, the system can request updated rules from an associated pharmaceutical entity, and can enforce the rules prior to the particular pharmaceutical being authorized to the patient. For example, the patient may be required to review information, watch a video, respond to questions, or take other actions as will be described. The system can subsequently update logs associated with the patient, for example update a blockchain based record as will be described.

The system, as will be described, can represent a medical network which can credit (e.g., authorize a patient to perform an action, such as obtain a pharmaceutical) or debit (e.g., indicate that the patient has performed the action, or de-authorize the credit) particular medical actions. As an example, upon a medical professional indicating that a patient is to receive a prescription, the system can update maintained information to indicate the patient's authorization. In this way, the system may optionally authorize patients to obtain pharmaceuticals based on received approval for associated prescriptions from medical professionals. Optionally, and as described above, the system may analyze medical history of the patient prior to the authorization. As will be described in more detail below, the system can optionally maintain information associated with each patient indicating a transaction record. In this specification, a transaction record includes any information indicative of authorizations or de-authorizations of prescriptions. The system can review the transaction record to ensure that the patient is not presently taking pharmaceuticals with contraindications to a potential prescription. Optionally, a transaction record can specify constraints associated with each prescription. Example constraints can include a number of pills of a pharmaceutical that the patient is authorized to receive, dosage, length associated with prescription, and so on.

Upon authorization of a prescription, and as described above, the system can update a transaction record associated with a patient. In this way, the system can ensure that a record of the authorizations is maintained. This authorization can propagate from the system to the patient, and optionally prescribing medical professional, such that the patient can utilize the authorization to obtain (e.g., fill) the prescription. As will be described, the system can generate an authorization token for storage by a user device of the patient, with the authorization token being utilized to confirm valid authorization for a particular pharmaceutical. As another example, the system can electronically sign information to be stored on the user device of the patient. For example, the system can utilize a public key/private key based signing scheme, such that outside systems (e.g., a pharmacy system) can ensure that the received information emanated from the system.

The authorization information can be utilized by a pharmacy as confirmation of the patient's prescription. As will be described, the patient's user device can execute an application (e.g., an electronic 'app' downloaded from an application store) to present authorized prescriptions to the patient. This application can receive information specifying authorized prescriptions from the system. Additionally, the application can store associated authorization information. To ensure that the application is only accessible by a specific patient, the application can require biometric authentication, password authentication, and so on.

Therefore, the patient can travel to a pharmacy, and utilize the application to obtain a pharmaceutical. For example, the patient can interact with his/her user device to provide authorization information to a system associated with the pharmacy. This authorization information, as described above, can confirm the patient's authorization to obtain an associated prescription. Subsequently, the application can update to indicate that the prescription has been filled. For example, the application can remove the prescription from a presentation of the patient's remaining prescriptions. In this way, the patient will be unable to access the prescription until a medical professional authorizes a new prescription.

Similarly, upon the pharmacy verifying that the authorization information is valid, the system can update to indicate that the prescription has been filled. For example, a transaction record of the patient can be updated to specify the filling of the prescription (e.g., a debit). With respect to the example of a blockchain, the system may include the transaction in the blockchain based network. In this way, the patient will be unable to utilize the prescription again. That is, the authorization information associated with the prescription will no longer be valid. Based on the updating of the transaction record, the system can provide information to the pharmacy rejecting the validity of any invalid the prescription. While the example of a blockchain is described above, it should be understood that a transaction record may be stored, or maintained, via different data storage techniques. For example, the system can store secure information in a database, such as structured or unstructured information.

Additionally, the system may store information indicative of authorized prescriptions, but not store potentially sensitive prescription information. For example, upon authorization of a prescription, the system can generate authorization information to be provided to a user device of a patient. The system can store information indicative of this authorization information, for example an encrypted hash of the information, a unique identifier, and so on. The authorization information stored by the user device of the patient may instead store (e.g., in an encrypted form) specific information associated with the prescription. For example, the specific information can include a name of the prescription, a number of pills, and so on. In this way, the patient can cause the decryption of the authorization information, and provide the specific information to the pharmacy. Example decryption schemes may be associated with proof of identity of the user, such as biometric identification, password, and so on. The pharmacy can then request that the system confirm the prescription is valid (e.g., the system can confirm the information indicative of the authorization information).

Optionally, a secret sharing scheme may be utilized with the system, user device, and/or pharmacy. As an example, an authorized prescription may be separated into a number of secret shares according to a secret sharing scheme. The system may retain a particular secret share, while providing a different secret share to the user device. The resulting secret (e.g., the prescription) may be generated upon a user being located at a pharmacy attempting to fill the prescription. For example, a pharmacy system associated with the pharmacy may receive the secret share from the patient's user device. In this example, the pharmacy system can provide the received secret share to the system. The system can then confirm the validity of the secret share, and generate the prescription. This secret can be provided to the pharmacy system, which can present the prescription to a pharmacist to fill. Optionally, the pharmacy system may receive both secret shares and generate the prescription.

While the description herein describes authorizing prescriptions, it should be understood that the system can be utilized for any medical equipment or necessity. For example, a medical professional can indicate that a patient requires use of a wheelchair. The system can then update to reflect that the patient is authorized for the wheelchair. This authorization may be utilized by a pharmacy, or other medical entity (e.g., medical equipment store), to provide the patient with a wheelchair. Additionally, the system may enable integration with medical payers, such that a cost associated with a prescription or medical equipment is automatically provided to a medical payer. As an example, the system can indicate to a pharmacy that a patient is authorized to obtain a particular pharmaceutical. The system can also provide information to a medical payer of the patient indicating that the patient is filling the pharmaceutical. The medical payer can then rapidly approve some, or all, of the associated cost of the prescription. This approval can be provided to the pharmacy, which may remove the approved portion of the cost from the patient's in-pharmacy bill.

The system described herein can therefore be utilized to overcome present technical hurdles associated with healthcare. For example, a patient can avoid being required to prove his/her identity, and the pharmacy can avoid requirements regarding confirming prescriptions with medical professionals. Instead, the patient can confirm his/her identity through interaction with the user device. For example, the patient can place a thumbprint on the user device as biometric confirmation that the user device belongs to the patient. As another example, the user device may determine a voice print, or other voice recognition information associated with a user of the user deice. In this example, biometric confirmation may be based on the user device successful determining that the voice print corresponds to the patient. Optionally, the user device may offload processing of the voice print to an outside system (e.g., via a network, such as the internet). Similarly, the user device can utilize facial recognition technology, and so on, to confirm the identity of the patient. Additionally, the system can confirm the validity of the authorization information such that medical professional confirmation is unnecessary.

However, for particular types of pharmaceuticals a medical professional may request that his/her confirmation be required prior to a pharmacy providing pharmaceuticals to a patient. For example, the system may receive information from a pharmacy requesting confirmation of a prescription. The system can then cause a prompt on the prescribing medical professional's user device requesting that the medical professional confirm the prescription. For example, the medical professional may be required to place his/her thumbprint on a reader. Upon this final authorization by the medical professional, the system can provide information to the pharmacy confirming the validity of the prescription.

FIG. 1A illustrates an example of a medical authorization system 100. The medical authorization system 100 can be a system of one or more computers, one or more virtual machines executed on a system of one or more computers, and so on. Optionally, the medical authorization system 100 may include virtualized processors, memory, storage systems, and so on, which may fluctuate according to demand. As described above, the medical risk authorization system 100 can receive requests 102 to authorize prescriptions, and generate transactions 112 in response to the requests 102. A transaction 112 may indicate approval of the request 102, or optionally denial of the request 102. For example, the transaction may specify a credit associated with a patient (e.g., an approved prescription). Additionally, a transaction 112 can include de-authorizing a previously authorized prescription (e.g., a debit). For example, a patient may have received a pharmaceutical associated with a prescription. In this example, the medical risk authorization system 100 can generate a transaction 112 indicating that the prescription is not valid.

FIG. 1A illustrates a pharmaceutical module 118 being provided to the medical risk authorization system 100. In some embodiments, the medical risk authorization system 100 can be configured according to a type of pharmaceutical. For example, prior to responding to requests 102 (e.g., as will be described), the medical risk authorization system 100 may be required to receive pharmaceutical module 118. This module 118 may then be loaded, for example into memory of the system 100. Optionally, the medical risk authorization system 100 may store multitudes of pharmaceutical modules. In this example, the medical risk authorization system 100 can receive selection of a pharmaceutical (e.g., from an outside system or user) and access the associated module. The pharmaceutical module 118 can cause different behavior of the system 100 according to the pharmaceutical associated with the module 118. In this way, the medical risk authorization 100 may not be configured to perform the functionality described herein absent the pharmaceutical module 118. Additionally, and as will be described, a patient's user device may obtain an application for execution on the user device. For example, the application may be obtained from an online 'app' store. Optionally, the application may be specific to a type of pharmaceutical. For example, the pharmaceutical module 118 executing on the medical risk authorization system 100 may be configured to only communicate with an application on a user device associated with a same pharmaceutical.

An example pharmaceutical module 118 may relate to opiates. In this example, the medical risk authorization system 100 may perform specific functionality related to opiates. Example functionality may include determining whether a patient being prescribed opiates has received opiates from other prescribers. For example, the medical risk authorization system 100 may analyze transactions 112 as will be described. Additional pharmaceutical modules may relate to thalidomide, lenalidomide, pomalidomide, and so on.

Thus, the particular pharmaceutical module 118 can cause varying behavior of the medical risk authorization system 100. With respect to an example pharmaceutical, the medical risk authorization system 100 may only authorize that the pharmaceutical is to be obtained from specific pharmacies. Additionally, the medical risk authorization system 100 may require that specific speech be presented to a patient upon authorization of the pharmaceutical. Optionally, the medical risk authorization system 100 may configure the systems that it communicates with. For example, FIG. 1B described below illustrates the medical risk authorization system 100 in communication with pharmaceutical entities (e.g., entity servers 150A-150N). These pharmaceutical entities may provide rules to the system 100 to enforce when authorizing a particular prescription. Example rules may include specific speech, or specific constraints (e.g., the patient may have to check in with a medical professional periodically). In this example, the particular pharmaceutical module 118 may limit the pharmaceutical entities which the system 100 is authorized to receive communications from.

A request 102 can specify that a particular patient is to be approved for a particular pharmaceutical. The system 100 can receive the request 102 from a user device or system associated with a medical professional. For example, a medical professional can examine a patient, and utilize a user device to specify information for a prescription to be provided to the patient. Optionally, the medical risk authorization system 100 may implement, or be in communication with, a web application utilized by the medical professional. The web application can present a user interface on the user device of the medical professional, which can enable a specification of a prescription. Optionally, the medical professional's user device may execute an application that presents a user interface enabling specification of a prescription.

As an example, the user interface can include textual fields for the medical professional to specify a name of a prescription. The medical professional may further specify constraints associated with the prescription. Example constraints may include a number of pills the patient is authorized to receive, a number of refills the patient can obtain, and so on. Optionally, constraints may indicate actions that the patient is to perform. For example, the medical professional can require that the patient weigh himself/herself periodically while taking the pharmaceutical. As another example, the medical professional can require that the patient measure blood glucose while taking the pharmaceutical. As will be described, the patient may therefore be required to perform the specified actions, and provide information to the medical risk authorization system 100 in response. The medical risk authorization system 100 can generate notifications to be provided to the medical professional, for example if the actions are not being performed. The medical authorization system 100 may further cause a prescription for same, or similar, pharmaceuticals to be de-authorized if the patient does not perform the actions.

Each request may be provided with information identifying a requesting medical professional. In this way, the medical risk authorization system 100 may ensure that requests 102 are being provided from authorized users with authority to grant prescriptions. For example, the medical risk authorization system 100 may store user account information for medical professionals. In this example, a medical professional can provide user account information, such as a user name and password, to the medical authorization system 100. As another example, the medical risk authorization system 100 may require biometric authorization from a medical professional. For example, the medical professional may be required to place his/her thumb on a thumbprint reader, or a facial recognition process may be required. Optionally, the medical professional's voice print (e.g., voice recognition) may be required. As will be described below, resulting transactions 112 may specify prescribing medical professionals, such that their prescriptions may be audited.

The medical risk authorization system 100 includes an approval engine 104 that can receive a request 102 and determine whether the request 102 is to be approved. As described above, optionally the medical risk authorization system 100 may automatically approve requests 102 received from medical professionals. That is, medical professionals may be assumed to understand risks associated with pharmaceuticals along with a patient's history. However, optionally the approval engine 104 can analyze medical information associated with a patient and identify whether a request 102 is to be authorized. In some embodiments, the approval engine 104 may access, or provide requests to, state databases. The state databases may be utilized to verify amounts of certain types of pharmaceuticals prescribed to a patient. Example pharmaceuticals may be opioid medications for a prescription drug monitoring program. Similarly, the state databases may verify amounts of certain types of pharmaceuticals prescribed by a medical professional. These amounts may be determined to exceed one or more limits, and thus a request may be denied.

Optionally, the medical risk authorization system 100 may have access to all of a patient's medical history. For example, the medical risk authorization system 100 may maintain information indicating locations at which each patient's medical history is stored. As patient's move between hospitals, private practices, emergency rooms, and so on, disparate medical records can be created by different medical professionals. The medical risk authorization system 100 may be able to securely access medical information stored on computers, servers, and so on, at each of these differing locations. As an example, a secure health protocol may be utilized that allows for such secure access to information. The medical risk authorization system 100 may therefore store information indicating locations at which to access a patient's medical history. In some embodiments, the medical risk authorization system 100 may provide a request for the patient's medical information to an outside system. The outside system may determine whether the patient has consented to the system 100 obtaining the patient's medical information. The outside system may also determine whether the patient has consented to a requesting medical professional providing medical care to the patient. For example, the patient may be required to indicate trust to the medical professional.

Optionally, the medical risk authorization system 100 can store some, or all of, a patient's medical history. That is, as differing medical professionals see a patient, the medical professionals can access a web application associated with the medical risk authorization system 100. The system 100 can therefore store the sensitive medical information, while optionally being able to access medical information stored locally on outside computer systems, servers, and so on. In this way, the medical risk authorization risk system 100 can review a patient's medical history while preserving the sensitive information to a requesting medical professional. For further description of a health protocol, and a system that enables such secure storage and access of medical information, see U.S. Patent Pub. 2018/0211059 which is incorporated by reference in its entirety.

Based on a patient's medical history, the approval engine 104 can determine whether a request 102 for a prescription is to be approved. For example, the approval engine 104 can analyze contraindications associated with a prescription and other pharmaceuticals being taken by the patient. As another example, the approval engine 104 can determine whether the patient has any allergies that may cause problems with the prescription. Since the medical risk authorization system 100 has access to a patient's medical history, the system 100 can identify any indications of allergies. In contrast, a medical professional may not be aware of certain allergies, or the patient may fail to mention them to the medical professional. As another example, the approval engine 104 can determine whether the prescription violates particular limitations associated with the prescription. Example limitations can include the patient being pregnant, younger than a certain age, having certain familial medical history, and so on.

For implementations in which the medical risk authorization system 100 does not have access to a patient's full medical history, the approval engine 104 can analyze prior transactions 112 associated with the patient. Since each transaction can indicate a particular prescription authorized for the patient, the approval engine 104 can identify all pharmaceuticals being utilized by the patient. Therefore, the approval engine 104 can determine whether a combination of the prescription with the currently utilized pharmaceuticals is associated with any contraindications. Furthermore, the approval engine 104 can identify whether the patient has exceeded prescriptions for a particular class of pharmaceutical. For example, the particular class may include opiates. As an example, a patient may attempt to obtain opiates from multiple medical professionals. As described above, the patient may visit emergency rooms, hospitals, and so on, in an attempt to obtain opiates while obfuscating the attempts from each medical professional. Since the patient's transactions 112 will, in this example, indicate that the patient has received prior prescriptions for opiates, the approval engine 104 can deny a request for additional opiates.

In this way, the approval engine 104 may determine whether the patient has exceeded one or more thresholds associated with a pharmaceutical (e.g., opiates). The engine 104 may, as described above, determine whether the patient has received greater than a threshold quantity of the pharmaceutical, or greater than a threshold in a certain time period. The engine 104 may also determine whether the patient has visited more than a threshold number of prescribing medical professionals (e.g., within a particular time period). The threshold may also relate to a threshold number of prescriptions given by a particular medical professional to patients. For example, if the medical professional has exceeded a threshold, the engine 104 may deny a request.

As will be described in more detail below, with respect to FIG. 1B, the medical risk authorization system 100 can be in communication with pharmaceutical systems. For example, the pharmaceutical systems can push rules to be enforced with respect to their pharmaceuticals. As described above, example rules can include particular speech being provided to the patient. Examples rule can also include particular speech provided to a medical professional. For example, speech to provide a patient or speech for the medical professional to receive. Example speech can include written information regarding a pharmaceutical, a video, a questionnaire, an interactive game confirming the speech was received and understood, and so on. Since the pharmaceutical systems can push information to the system 100, or optionally the system 100 can periodically pull information, the pharmaceutical systems can provide updated contraindications with respect to their pharmaceuticals. The approval engine 104 can utilize this real-time contraindication information to inform whether a request 102 is to be approved or denied. For example, a pharmaceutical company may have access to recent research regarding a pharmaceutical. To ensure that the approval engine 104 utilizes current, or fresh, information, the approval engine 104 can obtain a most recent version of the information from a pharmaceutical system.

Optionally, if the approval engine 104 denies a request 102, the medical risk authorization system 100 can provide information identifying the denial to a requesting medical professional. The medical professional can then cause an override of the denial, such that a prescription is authorized. The approval engine 104 can provide information indicating particular reasons why the request 102 was denied. For example, the approval engine 104 can specify that the patient is taking one or more contrary pharmaceuticals. As another example, the approval engine 104 can specify that the patient has exceeded a limit for a particular type of pharmaceutical, and so on.

The medical risk authorization system 100 includes a transaction engine 110 that can generate transactions 112 in response to approvals of requests 102. A transaction 112 can include information describing an approved request 102. For example, a transaction 112 can indicate that a particular patient is authorized to obtain a particular pharmaceutical with particular constraints. Similar to a credit being issued to, for example, a merchant indicating that a particular credited value has been authorized for the merchant, the transaction 112 can record an approved prescription request 102. In this way, a pharmacy or other requesting entity may query the medical risk authorization system 100 for confirmation of the validity of a prescription. The medical risk authorization system 100 can respond and indicate some, or all of, the information included in the transaction 112. Example information can include a name of a prescribing medical professional, a dosage associated with the prescription, a length of time associated with the prescription, constraints associated with the prescription, and so on. Optionally, the medical risk authorization system 100 can confirm that the transaction 112 was generated based on a request from a valid medical professional, but not indicate a name of the medical professional.

As illustrated in the example of FIG. 1A, the medical risk authorization system 100 is in communication with a transaction record information database 116. As will be described, the transaction record information database 116 can store transaction records associated with patients. As described above, a transaction record can include information specifying transactions associated with each patient, thereby generating a record of the prescriptions authorized to each patient. The transaction record information database 116 may be a database, a distributed database, a storage system, and so on. For example, the transaction record information database 116 can be a MySQL, NoSQL, and so on, database. Optionally, the database 116 may store objects associated with each patient, such as information included in JavaScript Object Notation (JSON). In this example, one or more transactions associated with each patient may each be encapsulated in a JSON file, with the included information specifying prescription information associated with the one or more transactions.

As described above, an example transaction 112 may specify a prescribing medical professional. An example transaction 112 may also specify a name of a pharmaceutical. An example transaction 112 may also specify a length of time to take the pharmaceutical. Additional information also be included in the example transaction 112. The transaction record information database 116 can therefore maintain these records for later access. For example, a pharmacy may access the transaction record information database 116. Additionally, the approval engine 104 may utilize the database 116 to determine whether to approve a received request 102. For example, the approval engine 104 can analyze prescriptions that are currently being taken by a patient. To identify such prescriptions, the approval engine 104 can determine which prescriptions are indicated as being active.

As an example, the approval engine 104 can identify all transactions associated with a patient, or transactions within a threshold period of time. The approval engine 104 can then filter the identified transactions according to a time at which the patient obtained the associated pharmaceuticals, and a length of time the patient is to take the pharmaceutical. As described above, a transaction 112 can indicate that a credit to a patient, that is that a prescription is authorized. Similarly, the transaction record information database 116 can store debit information, indicating that a prescription has been filled or is no longer valid. In this way, the approval engine 104 can determine a time at which the prescription was filled, and can then identify currently active prescriptions. Optionally, the approval engine 104 may provide requests to an application executing on a user device of a user. This application may store information indicating prescriptions being utilized by a patient operating the user device. Thus, the approval engine 104 can identify currently active prescriptions. Additional information related to the application is described in more detail below.

The transaction record database 116 may optionally be implemented as a blockchain storing transaction information. Since a transaction can include a prescription being authorized, or de-authorized, to a patient, the blockchain can maintain a record associated with all authorized prescriptions. The medical risk authorization system 100 can therefore receive a request from a pharmacy regarding validity of a prescription, and utilizing the blockchain can determine whether the prescription is still authorized. Optionally, the blockchain network may be accessible to outside systems, such as systems associated with pharmacies. These systems may receive authorization information from user devices of patients, and based on the authorization information may access the blockchain network to determine whether the associated prescription is valid. For example, the authorization information may specify encrypted hash information associated with an initial transaction generated in response to approval of a prescription. These outside systems may analyze the blockchain network to determine whether any subsequent transactions associated with the encrypted hash information caused the prescription to be invalid. In this way, the validity of a prescription can be rapidly identified via an automatic lookup of the blockchain network.

As a patient utilizes his/her prescription, the patient may obtain one or more refills. For example, a medical professional may prescribe a particular number of refills (e.g., 3, 4, and so on). The blockchain may thus reflect a transaction that indicates a refill. For example, a pharmacy system (e.g. system 140 described below) may provide a transaction indicating the refill. As will be described below, the patient's user device may transmit authorization information 114 associated with the prescription to the pharmacy. If the patient requests a refill, the pharmacy system may analyze the blockchain to identify a number of refills associated with the prescription. The pharmacy system can then issue another transaction indicating a new refill if the patient has remaining refills. Optionally, the issued transaction may be analyzed by a smart contract or oracle. For example, the oracle may determine that the pharmacy system is authorized to issue transactions. The oracle may then provide information to a smart contract associated with the blockchain network. The smart contract can cause generation of a new block, or a transaction within a proposed block, recording the refill. Example information to record may include a unique identifier associated with the prescription. The information may further include a unique identifier associated with the application executing on the patient's user device. In some embodiments, a unique identifier associated with the patient may be recorded. In this way, the blockchain may record the prescription information of a plurality of patients.

Figure 1B:
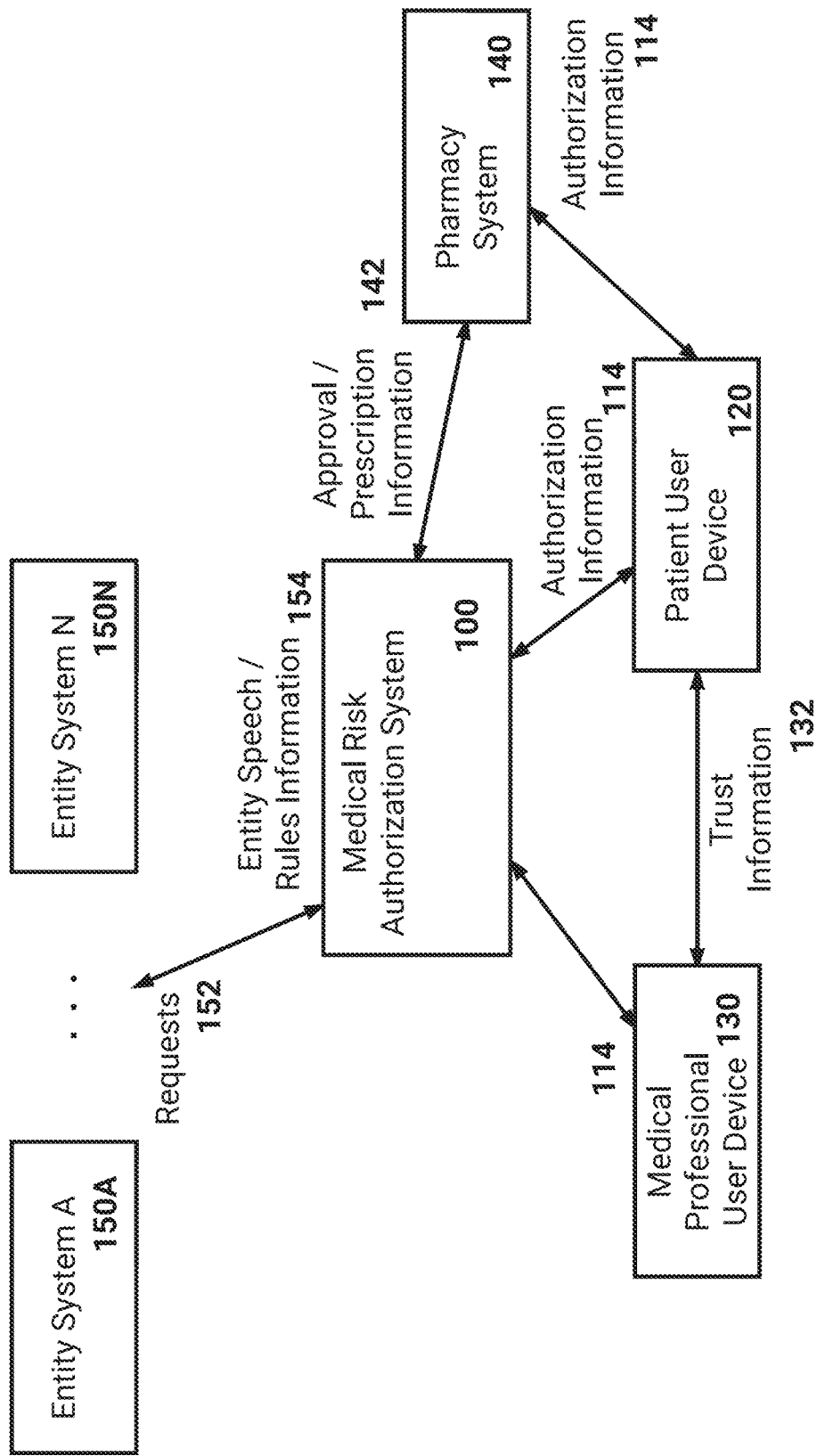
FIG. 1B illustrates an example of a medical authorization system in communication with outside systems.

FIG. 1B illustrates an example of a medical authorization system 100 in communication with outside systems. As described above, with respect to FIG. 1A, the medical risk authorization system 100 can respond to requests for approval of prescriptions, and generate transactions recording approved prescriptions. As illustrated in FIG. 1B, the medical risk authorization system 100 can be in communication with a medical professional user device 130, a patient user device 120, a pharmacy system 140, and/or entity systems A-N 150A-150N. Examples of an entity system can include a pharmaceutical company system, a medical payer system (e.g., insurance system), and so on. Via automated interactions with each of the outside systems, the medical risk authorization system 100 may enable, at least in part, the technical benefits described herein.

As illustrated, trust information 132 is indicated between the medical professional user device 130 and the patient user device 120. Trust, as described above, can represent that a patient confirmed a medical professional is authorized to access medical information associated with the patient. For example, upon meeting with a medical professional for a first time, the patient can utilize his/her user device 120 to provide trust to the medical professional 130. As an example, the patient can confirm his/her identity on the user device 120. An application executing on the user device 120 can confirm that trust is to be established with the medical professional. Optionally, the patient can consent to a trust relationship. The trust relationship can be associated with a group of medical professionals, for example at a hospital or other medical provider.

The trust information 132 can be utilized by the medical risk authorization system 100 to confirm that the medical professional is authorized to access medical information of the patient. Additionally, the trust information 132 can be utilized to record uniquely identifying information associated with the patient user device 120. For example, when the medical risk authorization system 100 provides authorization information 114 confirming a prescription to the patient user device 120, the trust information 132 can be utilized to confirm that the patient user device 120 belongs to the patient. Further description related to trust information 132 is described in U.S. Patent Pub. 2018/0211059, which is incorporated by reference in its entirety.

As described in FIG. 1A, the medical risk authorization system 100 can approve requests 152 for prescriptions. Upon approval of a received request associated with a patient, the medical risk authorization system 100 can generate authorization information 114 to be provided to the patient's user device (e.g., device 120). In implementations in which trust information 132 is maintained, the medical risk authorization system 100 can identify a particular patient user device 120 to receive the authorization information 114 based on an identity of the prescribing medical professional and patient. For example, the system 100 can identify a medical professional indicated in the request to authorize a prescription. The system 100 can then obtain an indication of a patient as specified in the request. The system 100 can determine whether the patient has indicated trust to the medical professional. Upon a positive determination, the system 100 can obtain unique identifying information associated with a user device utilized to indicate trust to the medical professional. The system 100 can then provide the authorization information 114 to the identified user device. In implementations in which trust information 132 is not utilized, the system 100 can store user account information associated with patients. Based on an identity of a patient specified in a request from the medical professional user device 130, the system 100 can access user account information associated with the patient. Subsequently, the system 100 can provide the authorization information 114 to an application associated with presentation of prescription information on the patient user device 120. For example, the system 100 can push the authorization information 114 to a user account associated with the patient. The patient user device 120 can then receive the information 114.

Optionally, the medical risk authorization system 100 can provide the authorization information 114 to the medical professional user device 130. An application executing on the user device 130 can then provide the authorization information via a local network to the patient user device 120. For example, the medical professional user device 130 can identify user devices within a threshold range, such as via Bluetooth, Near Field Communications, a locally generated Wi-Fi network, and so on. The medical professional user device 130 can then provide the authorization information 114 to an application executing on the patient user device 120. In this way, the authorization information 114 is substantially guaranteed to be provided to the correct patient's user device 120.

Example authorization information 114 can include an authorization token, such as an OAuth token, a JSON token, and so on. In the example of an OAuth token, the authorization information 114 can enable a third party to access a portion of a transaction record associated with the patient. For example, the authorization information 114 can be provided to a pharmacy system 140, which can utilize the authorization information 114 to verify the validity of the associated prescription. As an example with respect to an OAuth token, the pharmacy system 140 may provide the OAuth token to the medical risk authorization system 100. Since the token authorizes the third party, which in this example is the pharmacy system 140, to access information associated with the prescription, the medical risk authorization system 100 can respond confirming or denying the prescription.

Additional authorization information 114 may include electronically signed information according to a public key/private key scheme. For example, the authorization information 114 can describe a prescription authorized to a patient utilizing the patient user device 120. This description can be signed according to a private key associated with the medical risk authorization system 100. The pharmacy system 140 can receive the electronically signed information, and confirm that the information is signed by the medical risk authorization system 100 according to a public key of the system 100. In this way, the pharmacy system 140 can be assured that the system 100 validly issued the prescription.

However, with the electronic signing scheme described above, the prescription may not have assurances that it is still valid. For example, the prescription may have been revoked by a medical professional, or the prescription may have been filled. Therefore, optionally the electronically signed information can specify a unique identifier associated with the prescription. The pharmacy system 140 can provide this unique identifier to the medical risk authorization system 100. Upon receipt, the medical risk authorization system 100 can analyze a transaction record associated with the patient, and ensure that the unique identifier is still valid. Similarly, this unique identifier may be analyzed based on a blockchain (e.g., as described in FIG. 1A). For example, transactions within the blockchain may be analyzed to determine whether the prescription was de-authorized.

The pharmacy system 140, as illustrated, can therefore receive approval/prescription information 142 from the medical risk authorization system 100 confirming that a prescription is valid. Optionally the information 142 can describe a prescription, such as a name of a prescribing medical professional, a name of an associated pharmaceutical, constraints associated with the pharmaceutical, and so on. For example, the authorization information 114 may be an authorization token associated with a prescription, and the system 100 can provide the specific prescription information to the pharmacy system 140. In this way, the medical authorization system 100 can be the only system authorized to describe specifics of prescriptions. Optionally the information 142 can indicate approval of a particular prescription, but not include specifics of the particular prescription. In this example, the patient user device 120 may provide specifics of a prescription to the pharmacy system 140. For example, the specific information may be electronically signed by the medical risk authorization system 100. The system 100 can therefore confirm that the prescription is still authorized to the patient. A pharmacist utilizing the pharmacy system 100 can thus fill the prescription according to the signed information received from the patient user device 120.

An entity system 150, such as a pharmaceutical company system, can define rules 154 associated with their pharmaceuticals. An example rule 154 may include the presentation, or otherwise providing of, particular speech to a patient or medical professional. For example, the patient may be required to read particular text. The patient may also be required to watch a video. The patient may also be required to have a discussion with his/her medical professional or pharmacist. The patient may also be required to respond to a questionnaire, play a game associated with the speech, and so on.

The rules 154 may be utilized by the medical risk authorization system 100 to enforce the speech that the pharmaceutical company indicates as being required for utilization of particular pharmaceuticals. To generate these rules 154, particular templates may be utilized by an entity system 150. An example template may specify particular text to be presented on a patient user device 120, or specify a location (e.g., network address) at which particular text is located. Similarly, an example template may specify video to be presented. An example template may further be associated with interactive user interface information. Example interactive user interface information may include questionnaires, interactive games describing risks and benefits of a pharmaceutical, and so on.

As illustrated in FIG. 1B, the medical risk authorization system 100 may provide a request 152 to an entity system 150A. The request 152 may be related to speech for one or more pharmaceuticals. For example, the request 152 may be a request for speech information 154 associated with a prescribed pharmaceutical for a patient. The medical risk authorization system 100 may optionally cache speech information 154, or may provide a request to a pharmaceutical company system 150A subsequent to each authorized prescription. In this way, the system 100 can be assured that up-to-date speech information 154 is presented to a patient user device 120. The speech information 154 can then be presented via an application executing on the patient user device 120.

Optionally particular rule information 154 may be specified indicating constraints associated with a prescription. For example, the rule information 154 can specify actions that a patient is to perform while taking a pharmaceutical. As an example, the patient may be required to utilize his/her mobile device to obtain an image of pills being consumed. In this way, dosage may be tracked. For example, a user device of the patient may monitor an amount of pills remaining in a current bottle. If the patient does not obtain pictures of the pills being consumed, or a video of swallowing, then the system 100 may de-authorize subsequent refills. Optionally, the system 100 may cause notifications to be triggered to a prescribing medical professional regarding pills not being taken.

As another example, an example action can include requiring that the patient weigh himself/herself, measure particular biometric markers, and so on. This rule information 154 may then be enforced by the medical risk authorization system 100. For example, the medical risk authorization system 100 can store the rule information 154 (e.g., in the transaction record information database 116). The medical risk authorization system 100 can then monitor conformity of the patient's actions to the rule information 154. With respect to the example of the patient weighing himself/herself, the patient can be required to enter weight measurements into an application executing on the patient's user device 120. Optionally, the application may communicate (e.g., via Bluetooth, or near field communi) with a smart scale. Optionally, the medical risk authorization system 100 can receive these measurements, and store them as being associated with a medical history of the patient. For example, in implementations in which the medical risk authorization system 100 maintains, or is able to locate, medical information of each patient as described above. Optionally, the medical risk authorization system 100 can receive metadata from the patient user device 120 confirming that a weight measurement was performed by the patient. This metadata may not include specific medical information, but be utilized to determine conformity with the rule information 154. The sensitive medical information may be stored by the patient's user device 120, and optionally shared directly with a medical professional.

In addition to an entity system 150A specifying rule information 154, a medical professional can further indicate constraints. For example, the medical professional can indicate actions that a patient is to perform when providing a request to authorize a prescription. For example, the medical professional can require that the patient check-in periodically with the medical professional while taking a pharmaceutical.

Adherence to this rule information 154 may inform approvals of prescriptions for patients. For example, if a patient is determined not to be performing actions indicated by the rule information 154, the medical risk authorization system 100 can deny requests for similar pharmaceuticals. As an example, the medical risk authorization system 100 can provide information to a medical professional that a patient has not been following the rule information 154. Additionally, the medical risk authorization system 100 may cause an authorized prescription to be de-authorized based on failure of a patient to adhere to the rule information 154. For example, an authorized prescription may indicate that a patient has a number of refills of a pharmaceutical. If the system 100 determines that the patient is not conforming to the rule information 154, the system 100 may cause remaining refills to be de-authorized. In this way, if a pharmacy system 140 attempts to validate the prescription, the system 100 can indicate that the prescription is no longer valid. Optionally, the system 100 may provide information to the medical professional user device 130 indicating that a patient is not performing required actions. The medical professional can be required to confirm that a prescription is to be de-authorized.

Optionally, the medical risk authorization system 100 may optionally be associated with only specific pharmacies. For example, one or more systems 100 may be utilized, with each system working with specific pharmacies. In this way, each pharmacy may be able to confirm prescriptions of patients that utilize the pharmacy, but outside pharmacies may be unable to fill the prescriptions.

FIGS. 2A-3B illustrate example user interfaces presented on patient user devices. The user interfaces can be examples of interactive user interfaces generated by applications executing on the user devices. For example, the applications may be obtained from electronic application stores, and may be associated with healthcare of users of the user devices. As another example, the user interfaces may be generated, at least in part, via web applications executing on outside systems. The user devices may access the web applications, and present (e.g., render) user interface information received from the web applications. As will be described, the user interfaces can enable a healthcare wallet. The healthcare wallet may allow a user to review authorized prescriptions. The healthcare wallet may also confirm that a prescription is to be filled. The healthcare wallet may also cause, or otherwise enable, payment of a filled prescription to be provided. As an example, payment may be obtained from an electronic wallet on a patient's user device. For example, payment may be obtained from a wallet enabling access to credit card or debit card information of the patient. The wallet may also optionally enable payment directly via an outside entity (e.g., an insurance company).

Figure 2A:
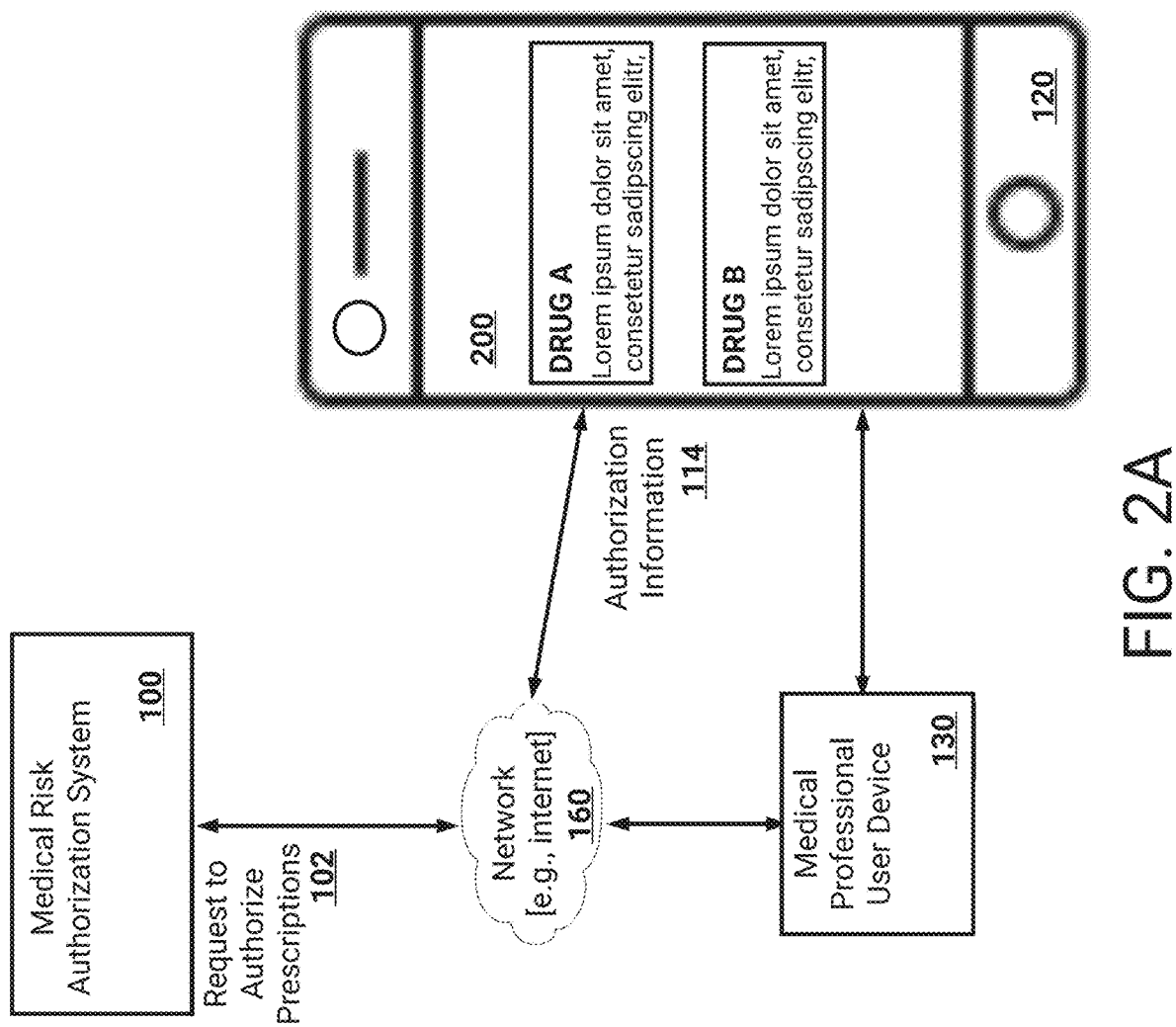
FIG. 2A illustrates an example user interface presenting authorized prescriptions of a patient.

FIG. 2A illustrates an example user interface 200 presenting authorized prescriptions of a patient on a user device 120 of the patient. As described above, with respect to FIGS. 1A-1B, the medical risk authorization system 100 can receive requests 102 to authorize prescriptions, and generate transaction information in response. Additionally, the medical risk authorization system 100 can provide authorization information 114 to the patient's user device 120 confirming validity of the requested prescription.

As illustrated in FIG. 2A, the medical risk authorization system 100 is illustrated as being in communication with a medical professional user device 130 via a network 160 (e.g., the internet). The system is also illustrated as being in communication with the patient's user device 120 via the network. Optionally, the network 160 may utilize a health communication protocol as described above. Based on approval of a request 102, the patient's user device 120 can receive authorization information 114 that is specific to an approved prescription.

For example, the user interface 200 includes two prescriptions, Drug A and Drug B. Each of the prescriptions includes textual information associated with the Drug A and Drug B. This textual information may specify constraints associated with the prescription, such as actions that a patient is to perform, a number of remaining refills, a time to take the prescription, and so on. This information may be received from the medical risk authorization system 100, for example as described above. Additionally, the user interface 200 may include information obtained from public databases that can be utilized by the patient to review detailed information associated with each prescription. As will be described below, with respect to FIG. 2B, a patient operating the user device 120 can interact with the user interface 200 to fill a prescription. For example, the patient can fill the prescription while located at a pharmacy.

In some embodiments, the user interface 200 may present locations at which each pharmaceutical is available to be filled. For example, the patient's insurance information may be accessed. Pharmacies which accept this insurance may then be presented. Additionally, the user device 120, or system 100, may provide functionality to enable a least cost routing. For example, the user interface 200 may present pricing information associated with each pharmaceutical. The pricing information may be obtained from pharmacies at which the pharmaceutical is available. Optionally, the user interface 200 may present both branded and generic versions of each drug. The user interface 200 may then present information indicating whether the patient's insurance covers each version. Pricing information may further be reflected. For example, the user interface 200 can indicate that a branded version of 'Drug A' costs a certain amount. The certain amount may include a cost per dose, a cost to utilize all of the prescription, and so on. The user interface 200 may also indicate costs for any generic versions of 'Drug A'. In this way, the patient using user interface 200 may select a choice associated with a preferred version of a pharmaceutical.

Figure 2B:
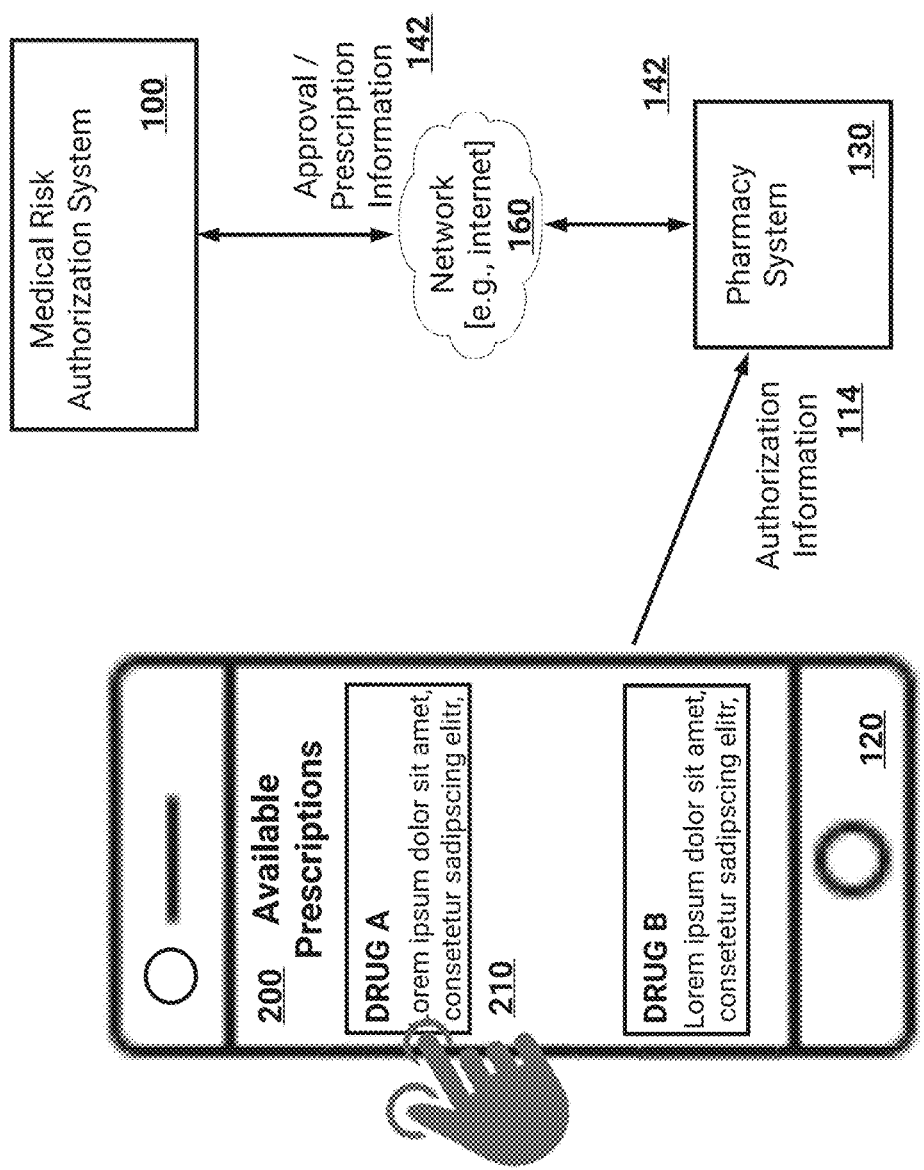
FIG. 2B illustrates an example user interface to fill an authorized prescription.

FIG. 2B illustrates an example user interface 200 to fill an authorized prescription. As described above, a patient can interact with the user interface 200 to specify a particular prescription that is to be filled. For example, the patient may be at a pharmacy to fill a particular prescription 210 (e.g., Drug A). The patient can select the particular prescription 210, and the user device 120 can provide associated authorization information 114 to a pharmacy system 130. For example, and as described above, the user device 120 can provide an authorization token, electronically signed information, and so on, to the pharmacy system 130. Optionally, the patient may be required by the user device 120 to confirm his/her identity. For example, the patient may be required to utilize a thumbprint reader, or the user device can utilize facial recognition technology to confirm the patient's identity.

Optionally, the patient's user device 120 may obtain location information associated with the user device 120. The user device 120 may then utilize the location information to confirm that the user device 120 is located at a pharmacy. Example location information can include global navigation satellite system coordinates. For example, upon the patient indicating that the particular prescription 210 is to be filled, the patient's user device 120 can ensure that the device 120 is located at a branch of a pharmacy corresponding to the pharmacy system 130. If the user device 120 determines it is located within a threshold distance of a pharmacy, the user device 120 can provide the authorization information 114 to the pharmacy system 130. Similarly, the patient's user device 120 may provide authorization information 114 via a local network, such as Bluetooth, Near Field Communication, and so on, to the pharmacy system 130. In this way, it may be substantially guaranteed that the user device 120 is physically present within a threshold distance of the pharmacy system 130.

In some implementations, the authorization information 114 may be provided to a particular pharmacy selected by the patient, prior to the patient entering the pharmacy. For example, the patient can operate the user interface 200 to select that the particular prescription 210 is to be filled. The user interface 200 can then present pharmacies that can fill the particular prescription 210, and optionally pharmacies near the patient or pharmacies generally utilized by the patient. The user device 120 can receive a selection of a pharmacy, and the user device 120 can provide the authorization information to a pharmacy system 130 associated with the pharmacy. In this way, the pharmacy may begin preparing the order automatically. Additionally, the pharmacy may prepare the order based on confirmation that the prescription is valid.

Optionally, the authorization information 114 may enable an automatic opening up of a securely locked cabinet storing a filled prescription. For example, a pharmacy may fill the particular prescription 210, and place the associated 'Drug A' in a locker within the pharmacy. The patient may then enter the pharmacy, and with his/her user device 120 can provide the authorization information to the pharmacy system 130. This pharmacy system 130 may confirm the validity of the prescription with the medical risk authorization system 100 as described above. Upon receipt of approval/prescription information 142, the pharmacy system 130 can cause the opening up of a secure lock. For example, the secure lock may be a smart lock. Additionally, the patient may interact with the user interface 200 to specify the particular prescription 210 while located proximate to lockers included in the pharmacy. A locker that includes 'Drug A' may automatically then open, for example based on the authorization information 114 being confirmed with the pharmacy system 130. To ensure that the patient is located at the pharmacy, as described above the user device 120 can be required to confirm its present location is within a threshold distance of the pharmacy. Additionally, the user device can provide the authorization information 114 via a local network, such as Bluetooth or near field communications. In this way, patients can automatically obtain prescriptions without interacting with a pharmacist.

However, pharmacists may prefer explaining each pharmaceutical to a patient. Therefore, if the patient can automatically obtain a prescription without interacting with a pharmacist, particular speech may therefore not be presented to the patient. Thus, optionally particular pharmaceuticals may be required to be picked up directly from a pharmacist. Optionally, prior to a patient being allowed to open a locker, the patient's user device 120 may be required to present textual information or video information describing the particular prescription 210. For example, the patient may be required to watch a video and optionally respond to a questionnaire, prior to a locker opening.

Figure 3A:
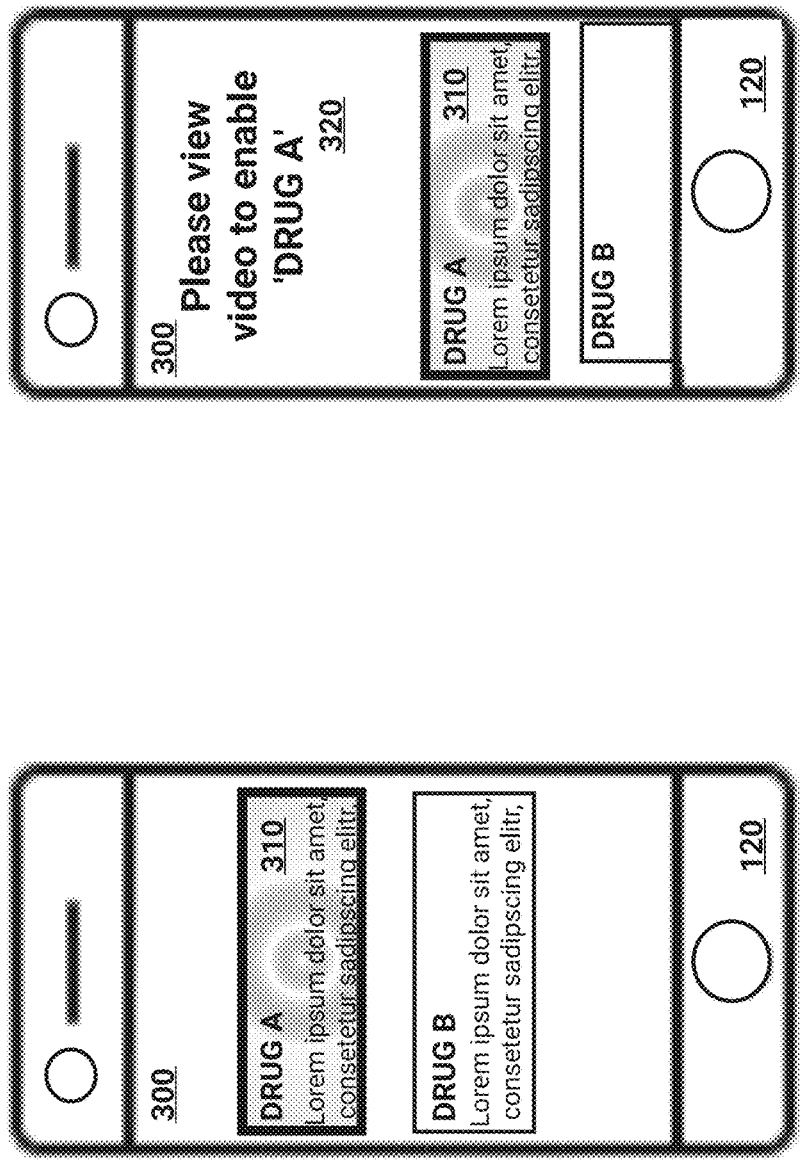
FIGS. 3A-3B illustrate speech associated with a prescription being provided on a user device of a patient.
Figure 3B:
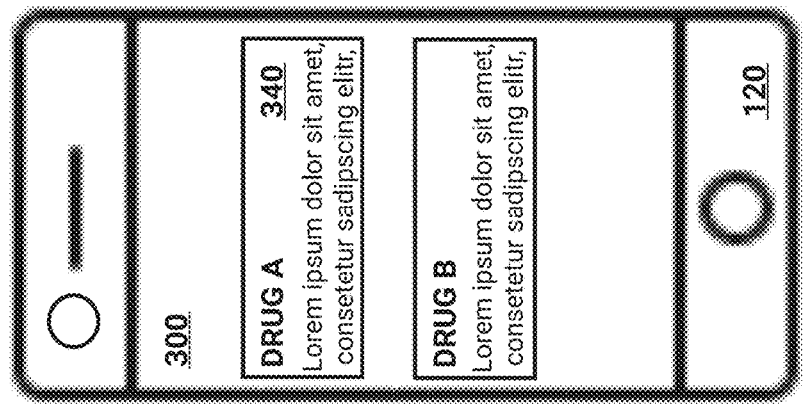
Figure 3B:
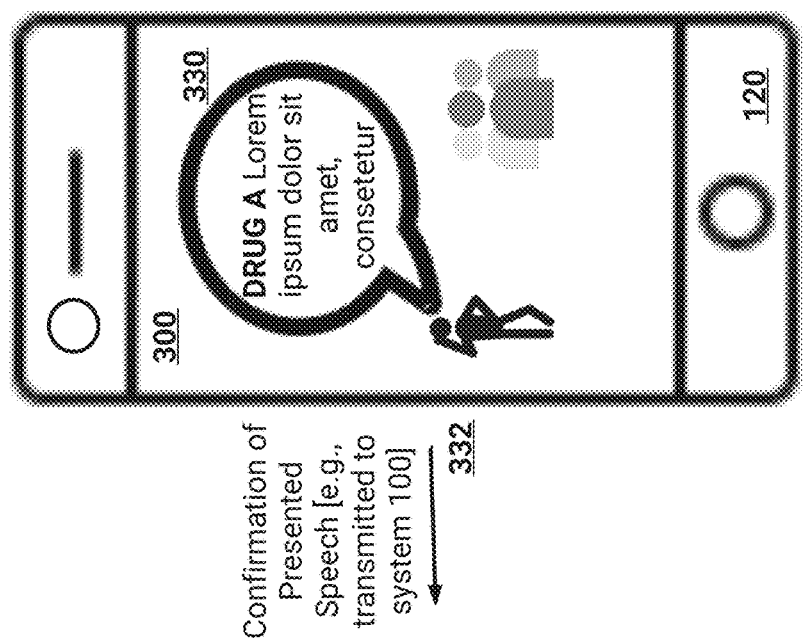

FIGS. 3A-3B illustrate speech associated with a prescription being provided on a user device of a patient. As described above, information for a prescription that is authorized for a patient may be presented on a user device 120 of the patient. However, particular prescriptions may be associated with constraints that need to be satisfied prior to the prescription being authorized to be filled by a pharmacy. As an example, a patient may be required to hear, view, or discuss with a medical professional or pharmacist, particular information.

As illustrated in FIG. 3A, a particular prescription 310 is indicated as not being ready to be filled. For example, the presented prescription can be shaded, colored, highlighted, and so on, to indicate that actions need to be performed. The medical risk authorization system 100 can enforce constraints associated with speech. The system 100 can provide authorization information 114 to the patient's user device 120, and if there are constraints associated with the prescription, can include the constraints in the authorization information. In this way, an application executing on the user device 120 can enforce the constraints and adjust the presented user interface 300.

In the example of FIG. 3A, the user interface 300 indicates that the patient is required to view a particular video associated with a prescription. For example, textual information 320 is included in the user interface 300 explaining the constraints. Optionally, the user interface 300 may indicate education and/or medical information related to each pharmaceutical, such that the patient may understand which medications are for which ailment. While the example of FIGS. 3A-3B includes the patient being required to view a video, as described above different speech may be presented to the patient. For example, the patient's medical professional or pharmacist may be required to describe the associated pharmaceutical to the patient. Once the description is provided, the patient can interact with the user interface 300 to select the particular prescription 320. Optionally, the user device of the patient may obtain audio (e.g., via a microphone). The audio may be analyzed to determine whether the speech was provided. For example, the user device or medical risk authorization system 100 may analyze the audio. The user interface 300 can then update with user selectable options for the patient to confirm that he/she received the description.

FIG. 3B illustrates speech being presented to the patient on the patient's user device 120. As illustrated in FIG. 3A, textual information 320 is included in the user interface 300 indicating the patient is required to view a video. The user interface 300 can receive user interactions to initiate the video, for example the patient can select the particular prescription 310. Optionally, the patient can press with greater than a particular force to initiate the video, or press for greater than a threshold amount of time. As illustrated, a video 330 can then be presented on the user device 120. As described above, a location at which the video is accessible may be provided to the user device 120 from the medical risk authorization system 100, such that the video can be obtained (e.g., streamed) for presentation. Additionally, the medical risk authorization system 100 may stream, or cause streaming of, the video. For example, the medical risk authorization system 100 may cause a content network to stream the video.

Additionally, the user device 120 can monitor the playing of the video 330, and upon completion of the video 330, can provide confirmation information 332 to the medical risk authorization system 100. Optionally, the user device 120 can utilize a forward-facing camera to ensure that the patient is viewing the video, and can ensure that the audio and/or screen brightness are sufficient for viewing.

In some embodiments, the user device 120 may require that the user respond to particular questions related to the speech presented to the user. For example, the application executing on the user device may request that the user fill in a portion of a text. The portion may be related to the presented speech. Additionally, the user device may ensure that other applications, or other user interfaces, are also being presented by the user device. For example, it should be understood that an example user device (e.g., a tablet) may enable a user to present two applications side by side, or one in a smaller window (e.g., picture in picture). In this example, the user device 120 may ensure that only the speech is being presented via the user device (e.g., video 330).

The system 100 can then update a transaction record associated with the particular prescription 320 to indicate that it is authorized to be filled. The user interface 300 can then update to reflect that the particular prescription 340 is available to be filled. For example, the user device 120 can receive information from the medical risk authorization system 100 confirming that the particular prescription 340 is valid. As another example, the user device 120 can automatically update the user interface 300 upon determining that the video 330 was viewed.

The application executing on the user device may enable certain feedback, or other interactivity, with respect to pharmaceuticals the user is utilizing. For example, with respect to opiates the user may indicate feedback to inform effectiveness of usage. Additionally, the user may interact with the application to trigger a pharmacy to begin preparation of filling a prescription. For example, upon viewing particular speech (e.g., as described above), the user device may provide information indicating the user can obtain a prescription. The information may be optionally be provided directly to a pharmacy system (e.g., via a network). For example, the user device may obtain a network location associated with the pharmacy system. Additionally, the information may be provided to the system 100, and routed to the pharmacy system. Similarly, refills may be automatically be triggered. As described above, the user device may monitor a number of pills a patient has consumed and/or has remaining. Thus, the user device may detect when the number of pills is below a threshold and may trigger a pharmacy to prepare a new refill. The user device may then present information informing the user a time at which to drive to the pharmacy (e.g., based on traffic information, time information received from the pharmacy, and so on).

Figure 4:
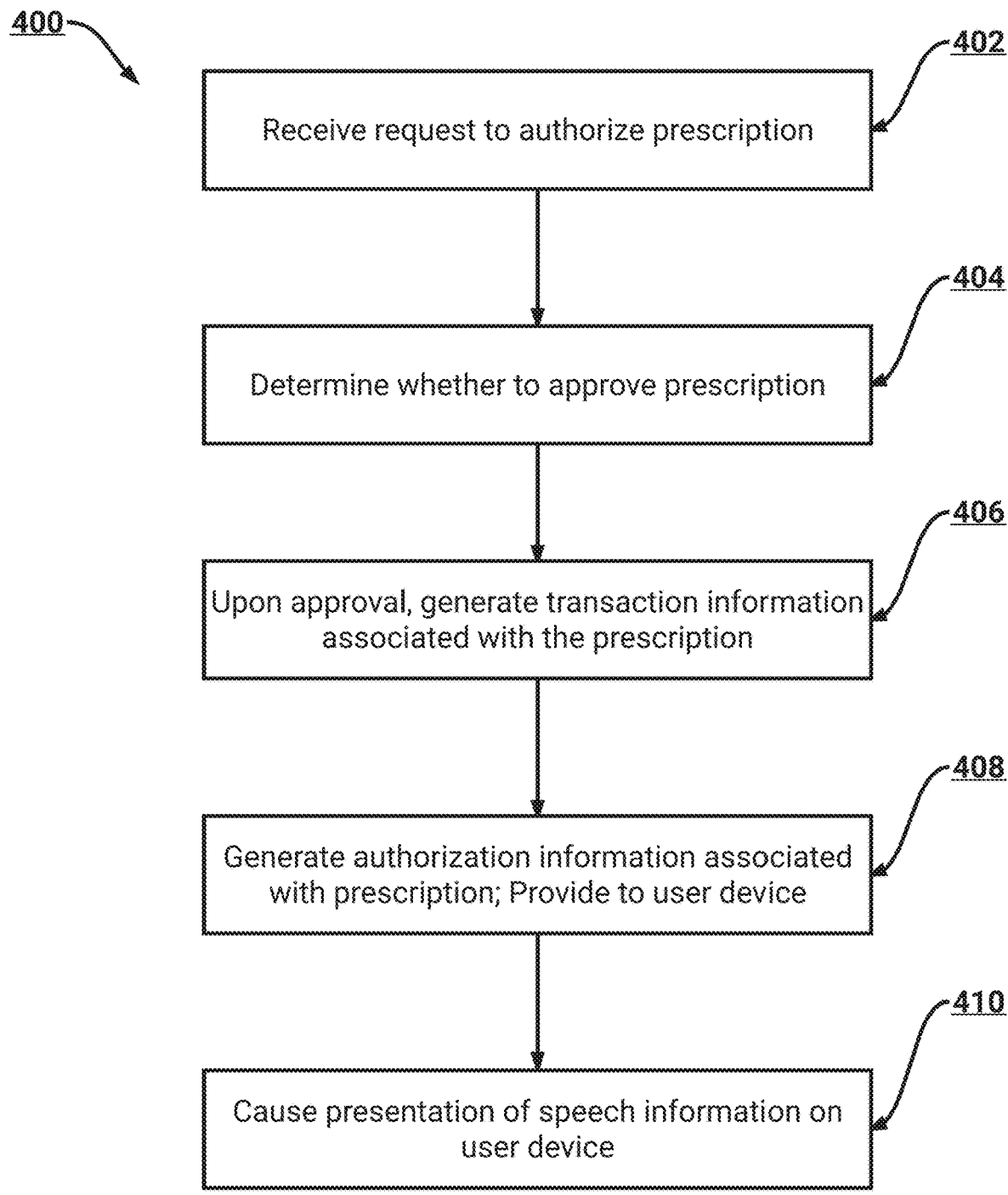
FIG. 4 is a flowchart of an example process for generating transactions in response to received prescriptions requests.

FIG. 4 is a flowchart of an example process 400 for generating transactions in response to received prescription requests. For convenience, the process 400 will be described as being performed by a system of one or more computers (e.g., the medical risk authorization system 100).

At block 402, the system receives a request to authorize a prescription. As described above, the system can receive requests from medical professional for approval of prescriptions. The system can ensure that the request is being received from valid medical professionals, and optionally from user devices known to be associated with the medical professionals.

At block 404, the system determines whether to approve the prescription. The system can optionally analyze medical history associated with a patient, to determine whether the patient would be at risk if the patient received the associated pharmaceutical. For example, the system can determine whether the patient has any illnesses or allergies that may cause risk with the pharmaceutical. Additionally, the system can analyze a transaction record associated with the patient to determine whether the patient is taking pharmaceuticals that may have contraindications with the prescription.

At block 406, the system generates transaction information associated with the prescription. Upon approval of the prescription, the system can generate transaction information confirming the prescription and associated information. For example, the transaction information can specify a name of the pharmaceutical, constraints associated with the pharmaceutical, and so on.

At block 408, the system generates authorization information associated with the prescription, and provides the information to a user device of the patient. As described above, the system can generate authorization information to be utilized to confirm that the prescription is valid. This authorization information can then be provided by the system to the patient's user device. For example, the system can push the authorization information to an application associated with user account information of a patient. For example, the patient can be logged into an application on his/her user device, and the system can push the authorization information to the application. Since the application is executing on the patient's user device, the user device can be ensured to be utilized by the patient.

The system causes presentation of speech information to the user device (block 410). The system can obtain rules associated with the patient, and cause presentation of the speech on the user device. As described above, with respect to FIGS. 3A-3B, the patient may be unable to utilize the prescription absent confirmation the speech was presented to the patient. A transaction may further be issued indicating that the prescription is authorized to be filled.

In some embodiments, the system may enable a third party to fill a prescription of the patient. For example, the system may store information identifying the third party. Example information may include a unique identifier associated with the third party, a name of the third party, and so on. If the third party travels to a pharmacy, the system may push authorization information to a system utilized by the pharmacy confirming the prescription. However, since this authorization information may be associated with the patient, the third party may be disallowed. Thus, in some embodiments the authorization information may specify the third party. Additionally, the third party may utilize an application associated with the system to request authorization. If the system determines the third party is authorized, the system can push information to the pharmaceutical system confirming the authorization.

Optionally, the third party may be reflected in a blockchain (e.g., as described above). In this example, identifying information associated with the third party may be stored in a block of the blockchain. Thus, the blockchain may be analyzed to determine whether the third party can fill the prescription. Optionally, the block may further specify types of pharmaceuticals the third party is authorized to fill and/or types they are not authorized to fill. Optionally, the patient may indicate that the third party is not authorized at a later point in time. Therefore, the blockchain may be analyzed to indicate whether the third party's authorization was revoked.

In some embodiments, the system may obtain, or otherwise link with, biometric information, electronic medical record systems, and so on to link with prescribing usage information of pharmaceuticals. The system, or an outside system, may aggregate this information to derive insights into outcomes of given therapeutics. For example, based on user responses entered into their user device regarding effectiveness (e.g., as described above). This information may be anonymized, thus ensuring privacy.

Additional Implementation Details and Embodiments

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

As described above, in various embodiments certain functionality may be accessible by a user through a web-based viewer (such as a web browser), or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A computer system comprising one or more computer processors configured to execute software code to perform operations comprising:

integrating a plurality of pharmaceutical modules associated with pharmaceuticals, the pharmaceutical modules being provided to the computer system via entity servers, and the pharmaceutical modules customizing functionality of the computer system, wherein the custom functionality indicates, at least, constraints associated with the pharmaceuticals;

receiving a request to authorize a prescription for a patient, the prescription being associated with a particular pharmaceutical, and the request being from a medical professional and the request being received via a network;

accessing a particular pharmaceutical module, of the plurality of pharmaceutical modules, associated with the particular pharmaceutical, and identifying one or more constraints associated with the particular pharmaceutical, the constraints being enforceable via the computer system;

generating a first transaction associated with the prescription, the first transaction indicating one or more credits and the one or more constraints, wherein the patient is authorized to access the credits to obtain an associated pharmaceutical based on satisfaction of the constraints, and wherein the first transaction is included in a transaction record associated with the patient;

generating authorization information associated with the prescription, the authorization information being provided to a user device of the patient, the authorization information including at least a subset of the constraints for enforcement by the user device, and the authorization information enabling confirmation by an outside system that the prescription is authorized;

cause presentation, via an interactive user interface on the user device, of speech information associated with the prescription, wherein upon confirmation of presentation of the speech information, the transaction record associated with the patient is updated to reflect satisfaction of the constraints; and receiving, from the outside system, a request for approval of the prescription and analyzing the transaction record, wherein in response to the transaction record indicating a remaining credit of the one or more credits and the satisfaction of the constraints, authorizing the request and generating a second transaction indicating a debit associated with the prescription, wherein the remaining credit is de-authorized.

2. The computer system of claim 1, wherein the request is authorized, and wherein authorizing the request comprises:
accessing the transaction record of the patient, the transaction record reflecting previously authorized prescriptions; and
identifying, based on the transaction record, that the patient has not exceeded one or more thresholds associated with the prescription.

3. The computer system of claim 1, wherein the request is authorized, and wherein authorizing the request is based on a medical history associated with the patient.

4. The computer system of claim 3, wherein accessing the medical history comprises:
obtaining information indicating servers at which portions of the patient's medical history is stored;
providing, via an application layer protocol, requests for the portions to an outside system, the outside system being configured to authorize requests based on trust information and route the requests to the indicated servers; and
receiving the portions from the outside system.

5. The computer system of claim 1, wherein the operations further comprise:
requesting, from one or more of the entity servers, current speech information associated with the prescription, wherein the entity servers define rules associated with presentation of the speech information;
receiving information indicating that an application executing on the user device has received user input associated with filling the prescription; and
transmitting the current speech information to the user device, the current speech information causing activation of the application.

6. The computer system of claim 1, wherein the authorization information comprises an authentication token, and wherein the user device is configured to provide the authorization information to the outside system based on biometric identification of the patient, the outside system being associated with a pharmacy filling the prescription.

7. The computer system of claim 1, wherein the speech information comprises a video presented via the user device.

8. The computer system of claim 1, wherein a first pharmaceutical module causes the computer system to communicate only with user devices executing a particular application associated with a first pharmaceutical, and/or wherein a second pharmaceutical module causes the computer system to constrain communications between the computer system and the entity servers to a subset of the entity servers authorized via the second pharmaceutical module.

9. A computer-implemented method comprising:
by a computer system,
integrating a plurality of pharmaceutical modules associated with pharmaceuticals, the pharmaceutical modules being provided to the computer system via entity servers, and the pharmaceutical modules configuring functionality of the computer system, wherein the configuring causes enforcement of specific constraints associated with the pharmaceuticals;
receiving a request to authorize a prescription for a patient, the prescription being associated with a particular pharmaceutical, and the request being from a medical professional and the request being received via a network;
accessing a particular pharmaceutical module, of the plurality of pharmaceutical modules, associated with the particular pharmaceutical, and identifying one or more constraints associated with the particular pharmaceutical, the constraints being enforceable via the computer system;
generating a first transaction associated with the prescription, the first transaction indicating one or more credits and the one or more constraints associated with the prescription, wherein the patient is authorized to access the credits to obtain an associated pharmaceutical based on satisfaction of the constraints, and wherein the first transaction is included in a transaction record associated with the patient;
generating authorization information associated with the prescription, the authorization information being provided to a user device of the patient, the authorization information including at least a subset of the constraints for enforcement by the user device, and the authorization information enabling confirmation by an outside system that the prescription is authorized;
cause presentation, via an interactive user interface on the user device, of speech information associated with the prescription, wherein upon confirmation of presentation of the speech information, the transaction record associated with the patient is updated to reflect satisfaction of the constraints; and
receiving, from the outside system, a request for approval of the prescription and analyzing the transaction record, wherein in response to the transaction record indicating a remaining credit of the one or more credits and the satisfaction of the constraints, authorizing the request and generating a second transaction indicating a debit associated with the prescription, wherein the remaining credit is de-authorized.

10. The method of claim 9, wherein the request is authorized, and wherein authorizing the request comprises:
accessing the transaction record of the patient, the transaction record reflecting previously authorized prescriptions; and
identifying, based on the transaction record, that the patient has not exceeded one or more thresholds associated with the prescription.

11. The method of claim 9, wherein the request is authorized, and wherein authorizing the request is based on a medical history associated with the patient.

12. The method of claim 11, wherein accessing the medical history comprises:
obtaining information indicating servers at which portions of the patient's medical history is stored;
providing, via an application layer protocol, requests for the portions to an outside system, the outside system being configured to authorize requests based on trust information and route the requests to the indicated servers; and
receiving the portions from the outside system.

13. The method of claim 9, further comprising:
requesting, from one or more of the entity servers, current speech information associated with the prescription, wherein the entity servers define rules associated with presentation of the speech information;
receiving information indicating that an application executing on the user device has received user input associated with filling the prescription; and
transmitting the current speech information to the user device, the current speech information causing activation of the application.

14. The method of claim 9, wherein the authorization information comprises an authentication token, and wherein the user device is configured to provide the authorization information to the outside system based on biometric identification of the patient, the outside system being associated with a pharmacy filling the prescription.

15. The method of claim 9, wherein the speech information comprises a video presented via the user device.

16. Non-transitory computer storage media storing instructions that, when executed by a system of one or more computers, cause the system to perform operations comprising:
    integrating a plurality of pharmaceutical modules associated with pharmaceuticals, the pharmaceutical modules being provided to the system via entity servers, and the pharmaceutical modules customizing functionality of the system, wherein the custom functionality indicates, at least, constraints associated with the pharmaceuticals;
    receiving a request to authorize a prescription for a patient, the prescription being associated with a particular pharmaceutical, and the request being from a medical professional and the request being received via a network;
    accessing a particular pharmaceutical module, of the plurality of pharmaceutical modules, associated with the particular pharmaceutical, and identifying one or more constraints associated with the particular pharmaceutical, the constraints being enforceable via the system;
    generating a first transaction associated with the prescription, the first transaction indicating one or more credits and the one or more constraints associated with the prescription, wherein the patient is authorized to access the credits to obtain an associated pharmaceutical based on satisfaction of the constraints, and wherein the first transaction is included in a transaction record associated with the patient;
    generating authorization information associated with the prescription, the authorization information being provided to a user device of the patient, the authorization information including at least a subset of the constraints for enforcement by the user device, and the authorization information enabling confirmation by an outside system that the prescription is authorized;
    cause presentation, via an interactive user interface on the user device, of speech information associated with the prescription, wherein upon confirmation of presentation of the speech information, the transaction record associated with the patient is updated to reflect satisfaction of the constraints; and
    receiving, from the outside system, a request for approval of the prescription and analyzing the transaction record, wherein in response to the transaction record indicating a remaining credit of the one or more credits and the satisfaction of the constraints, authorizing the request and generating a second transaction indicating a debit associated with the prescription, wherein the remaining credit is de-authorized.

17. The computer storage media of claim 16, wherein the request is authorized, and wherein authorizing the request comprises:
    accessing the transaction record of the patient, the transaction record reflecting previously authorized prescriptions; and
    identifying, based on the transaction record, that the patient has not exceeded one or more thresholds associated with the prescription.

18. The computer storage media of claim 16, wherein the request is authorized, wherein authorizing the request is based on a medical history associated with the patient, and wherein accessing the medical history comprises:
    obtaining information indicating servers at which portions of the patient's medical history is stored;
    providing, via an application layer protocol, requests for the portions to an outside system, the outside system being configured to authorize requests based on trust information and route the requests to the indicated servers; and
    receiving the portions from the outside system.

19. The computer storage media of claim 16, wherein the operations further comprise:
    requesting, from one or more of the entity servers, current speech information associated with the prescription, wherein the entity servers define rules associated with presentation of the speech information;
    receiving information indicating that an application executing on the user device has received user input associated with filling the prescription; and
    transmitting the current speech information to the user device, the current speech information causing activation of the application.

20. The computer storage media of claim 16, wherein the authorization information comprises an authentication token, and wherein the user device is configured to provide the authorization information to the outside system based on biometric identification of the patient, the outside system being associated with a pharmacy filling the prescription.

* * * * *